United States Patent [19]
Buser et al.

[11] Patent Number: 6,066,109
[45] Date of Patent: May 23, 2000

[54] PELVIC REDUCTION DEVICE

[76] Inventors: Byron Maxwell Buser; John Paul Buser, both of 837 Cornish Dr., San Diego, Calif. 92107

[21] Appl. No.: 09/162,252

[22] Filed: Sep. 28, 1998

Related U.S. Application Data

[63] Continuation-in-part of application No. 08/837,310, Apr. 9, 1997, which is a continuation-in-part of application No. 08/566,007, Dec. 1, 1995, abandoned.

[51] Int. Cl.$^7$ ............................... A61F 5/00; A61F 5/28; A61F 5/34
[52] U.S. Cl. ........................... 602/23; 602/13; 128/99.1; 128/118.1
[58] Field of Search ................................. 602/13, 19, 23; 606/201–204; 441/88, 91, 106, 108, 129; 128/876, 96.1, 99.1, 102.1, 106.1, 107.1, 118.1, DIG. 20; 2/465, DIG. 3, 311, 312, 44

[56] References Cited

U.S. PATENT DOCUMENTS

| | | |
|---|---|---|
| 2,552,475 | 5/1951 | Austlid . |
| 3,799,156 | 3/1974 | Gurkin . |
| 4,135,503 | 1/1979 | Romano . |
| 4,157,713 | 6/1979 | Clarey . |
| 4,178,923 | 12/1979 | Curlee . |
| 4,715,364 | 12/1987 | Noguchi . |
| 4,836,194 | 6/1989 | Sebastian et al. .......... 128/DIG. 20 X |
| 4,870,706 | 10/1989 | Ketcham et al. ........... 128/DIG. 20 X |
| 5,236,411 | 8/1993 | Backman . |
| 5,393,230 | 2/1995 | Vizintin et al. . |
| 5,407,421 | 4/1995 | Goldsmith . |
| 5,437,618 | 8/1995 | Sikes . |

OTHER PUBLICATIONS

Roy Sanders, MD et al, External fixation of the pelvis: Application of the resuscitation frame, pp. 60–64, Techniques in Orthopaedics, vol. 4, Issue 4, 1990.

David L. Helfer, MD, Open reduction internal fixation of the pelvis, pp. 67–78, Techniques in Orthopaedics, vol. 4, Issue 4, 1990.

Reinhold Ganz, M.D. et al., *The Antishock Pelvic Clamp*, pp. 71–78, Jun. 1991, Clinical Orthopaedics and Related Research.

*Primary Examiner*—Richard J. Apley
*Assistant Examiner*—Denise Pothier
*Attorney, Agent, or Firm*—Nydegger & Associates

[57] ABSTRACT

A method for anatomical reduction of the bones of the pelvis includes a belt having a clasp or other fastening member. The device also includes at least two inflatable bladders slidingly positionable along the belt. Operationally, the device is positioned to encircle the hips of a patient with a bladder positioned over each of the patient's hip bones. The clasp is fastened to hold the belt in place and a pump is used to selectively inflate each of the bladders. Inflation of the bladders applies a compressive force in excess of five hundred pounds to the pelvic bones of the patient reducing the intra-pelvic volume, thereby minimizing blood loss attributable to fractures or diastasis of the pelvis.

3 Claims, 2 Drawing Sheets

PELVIC REDUCTION DEVICE

This is a continuation-in-part application of application Ser. No. 08/837,310, filed on Apr. 9, 1997, which is a continuation-in-part application of application Ser. No. 08/566,007, filed on Dec. 1, 1995, which is now abandoned.

FIELD OF THE INVENTION

The present invention pertains to medical devices which are useful for the treatment of traumatic conditions. More particularly, the present invention pertains to medical devices which are appropriate for the treatment of fractures and diastases of the bones which form the pelvis. The present invention is particularly, but not exclusively useful as a compressive splint which can be applied to a patient to prevent internal bleeding due to traumatic injury of the pelvic bones.

BACKGROUND OF THE INVENTION

In the past, it has been recognized that traumatic injuries which involve the bones of the pelvis present a substantial risk to the health of the involved patient. In fact, it is not uncommon that injuries of this nature can be life-threatening or even fatal. In general terms, injuries to the pelvic bones may be classified as fractures, or injuries where the bones or the pelvis are actually broken, or diastasis, where adjacent bones are separated without actual breakage of the bones.

Regardless of whether a particular pelvic injury involves a fracture or diastasis, there is generally a substantial risk of associated internal bleeding. Internal bleeding of this type may be quite severe and, often, quite difficult to detect. As a result, there are many cases of patient mortality that result from internal bleeding caused by injury to the pelvic bones.

Practice has demonstrated that there are several effective techniques for control of internal bleeding resulting from injury to the bones of the pelvis. In fact, it is often the case that simple immobilization of the patient will often reduce internal blood loss, giving the attending medical personnel greater time in which to treat the effected bone structure. Unfortunately, total immobilization of the patient may be both impractical and undesirable. For example, it is often the case that a patient will need to be adjusted in a range of differing positions so that required X-ray images may be obtained. In cases where the patient has an injury to the bones of the pelvis, however, there is an ever present danger that each of these manipulations will result in increased internal bleeding and increased risk to the health of the patient.

Practice has also shown that blood loss associated with injury to the bones of the patient may be reduced by manual compression of the pelvis. For manual compression, an attendant, or attendants, manually apply pressure to the patient's hips, forcing the bones of the pelvis together and reducing blood loss in areas where the pelvic bones have separated. Generally, manual compression is useful when a patient must be positioned or manipulated during the process of obtaining X-rays. Unfortunately, there is a tendency for the attendant's protective gloves and hands to interfere with the X-ray imaging process. As a result, the quality of the X-ray images may be reduced, or the effectiveness of the manual compression may be compromised. Further, it is known that in order to effectively stop internal bleeding by compression will require forces of approximately five hundred pounds, or more.

Another technique that has been developed to reduce internal bleeding associated with injury to the bones of the pelvis is the use of a pelvic clamp. Clamps of this type generally resemble "C" clamps of the type used by carpenters. Unlike the carpenter's "C" clamp, however, pelvic clamps include a pair of rods, or screws, which are intended to be inserted into the innominate bone of the pelvis. Functionally, application of a pelvic clamp begins with insertion of the rods into the hip bones of the patient. Once the rods are inserted, the clamp applies pressure to each of the rods, compressing the bones of the pelvis against each other.

Use of the pelvic clamp has proven to be an effective method for reduction of internal bleeding. Unfortunately, there are a number of disadvantages which are generally associated with use of clamps of this type. For example, it is easily appreciated that application of the clamp is an invasive, traumatic procedure which requires the creation of large stab wounds for the insertion of the rods into the patient's hip bones. Additionally, the application of the clamp necessarily results in a certain degree of trauma to the innominate bone at the points where the rods are inserted. Application of the pelvic clamp also presents a risk of more serious injury to the patient. More specifically, it has been established that mis-insertion of the rods can result in damage to the nervous and vascular systems associated with the pelvis. In either case, there may be serious health implications for the involved patient. Further, a significant draw back of the "C" clamp is that it is not radio luscent. Finally, it is also the case that the pelvic clamp is itself a bulky apparatus which makes manipulation of the patient, as well as access to the patient, problematic. This is especially true where the desired course of treatment requires that the clamp be left in position during abdominal or pelvic surgery.

Unfortunately, due to the disadvantages inherent in the use of pelvic clamps, there is a tendency to restrict the use of clamps of this type to situations where the attending personnel have verified that an appropriate injury exists. Verification of such an injury may, of course, require additional time and thus delay or complicate treatment of the patient. The disadvantages inherent in the use of pelvic clamps also tend to limit their use to situations where an orthopedic surgeon or other highly-trained person is available to perform the procedure necessary for application of the clamp. In cases where an orthopedic surgeon is not available, application of the clamp may be delayed with possible negative health implications for the patient.

In light of the above, it is an object of the present invention to provide a non-invasive device for anatomical reduction of the pelvic bones of a patient which can generate compressive forces on the patient which are greater than five hundred pounds, and which may be applied to the patient with minimal traumatic side-effects. Another object of the present invention is to provide a device for anatomical reduction of the pelvic bones of a patient which does not interfere with subsequent manipulation of the patient. Another object of the present invention is to provide a device for anatomical reduction of the pelvic bones of a patient which may be left in-situ during surgical procedures involving the abdomen or the pelvis or during the gathering of required X-ray images. Still another object of the present invention is to provide a device for anatomical reduction of the pelvic bones of a patient which minimized the training required for proper usage. Yet another object of the present invention is to provide a device for anatomical reduction of the pelvic bones of a patient which is simple to use, relatively easy to manufacture and comparatively cost effective.

SUMMARY OF THE PREFERRED EMBODIMENTS

The present invention is a device for anatomical reduction of the bones of the pelvis. In general terms, the present invention includes a belt positionable around the hips of a patient. A pair of expandable bladders are slidingly mounted to the belt to be selectively positioned over the patient's hips. The combination of the belt and the bladders allows a compressive force to be applied to force the bones of the pelvis together thereby reducing or preventing internal blood loss associated with diastasis or fracture of the pelvic bones.

In greater detail, the present invention includes a flexible belt having a first end and a second end. The belt is preferably formed from a sterilizable material such as nylon webbing. The present invention also includes a connector or fastener attached to the first and second ends of the belt. The fastener allows the first and second ends of the belt to be quickly connected and disconnected. Additionally, the fastener allows the overall length of the belt to be adjusted. Generally, any type of connector which offers the combination of quick connectability and length adjustment may be utilized. For example, the first and second ends of the belt may be fabricated with complementary VELCRO type fasteners. Preferably, however, the fastener is fabricated as a two part quick-release clasp or buckle. When a fastener of this type is employed, the first part of the quick-release buckle is attached to the first end of the belt and the second part of the quick-release buckle is attached to the second end of the belt. Interconnection of the first part of the buckle and the second part of the buckle connects the first end of the belt to the second end of the belt. Additionally, the point of attachment of the first part of the buckle and the first end of the belt is adjustable to allow the overall length of the belt to be selected. Similarly, the point of attachment of the second part of the buckle and the second end of the belt is adjustable to allow the overall length of the belt to be selected.

The present invention also includes at least two bladders. Each of the bladders is substantially rectangular in shape and attached to the belt. The attachment between the bladders and the belt is of a sliding nature, similar in nature to the attachment of weights to a diver's belt. This allows the position of each bladder to be individually adjusted to any point between the first end and the second end of the belt. Each of the bladders is formed to surround a chamber. Additionally, each of the bladders includes a quick-release connector attached in fluid communication with the chamber. The quick-release connector is connectable to a pump, such as a hand-held bulb-type pump. The pump may then be used to selectively pressurize each chamber to selectively inflate and expand each of the bladders. As intended for the present invention, the result of this inflation is the creation of opposing compressive forces on the hips of the patient that can be in excess of approximately five hundred pounds (F>500 lbs).

In many cases, due to the strong forces involved and resultant high pressures on the skeletal structure of the patient, it will be desirable to include a pressure relief valve in each of the bladders. A valve of this type is configured to open when the pressure within the bladder reaches a predetermined level. In this fashion, the relief valve prevents over-pressurization of the bladders.

Operationally, the belt of the present invention is first positioned to encircle the hips of a patient. As the belt is positioned, an inflatable bladder is positioned over each of the patient's hip bones. The clasp is then used to attach the first end of the belt to the second end of the belt, holding the belt around the patient's hips. At the same time, the length of the belt is adjusted so that the belt is snug against the patient's body. Once the belt is snugly but not tightly secured around the patient, the pump is used to selectively inflate each of the bladders. Inflation of the bladders results in two interrelated but opposite effects. The first effect is to minimize or eliminate the forces which are otherwise applied by the belt against the abdomen and back when the bladders are deflated. Recall, there is no bladder positioned against either the abdomen or the back. Thus, as the bladders which are positioned under the belt and against the hips of the patient are enlarged, by inflation, the belt is effectively lifted from the body. Due to this lifting action, the forces of the belt against the abdomen and back are relived. On the otherhand, the opposing forces of the bladder and belt combination against the hips of the patient are greatly increased. This is the second effect. As indicated above, the magnitude of these opposing forces must be significant and will generally be in a range greater than five hundred pounds.

As each bladder is inflated, the combination of the inflating bladders and the belt applies a compressive force to the hips of the patient. The compressive force holds the bones of the pelvis together and reduces the intra-pelvic volume preventing excessive blood loss associated with pelvic fractures and diastasis. The magnitude of the compressive force is maintained at safe levels by the operation of the pressure relief valves which prevent over pressurization of the bladders. Once the device has been applied and properly inflated, the patient may be manipulated to obtain required X-rays, surgery and other treatment.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
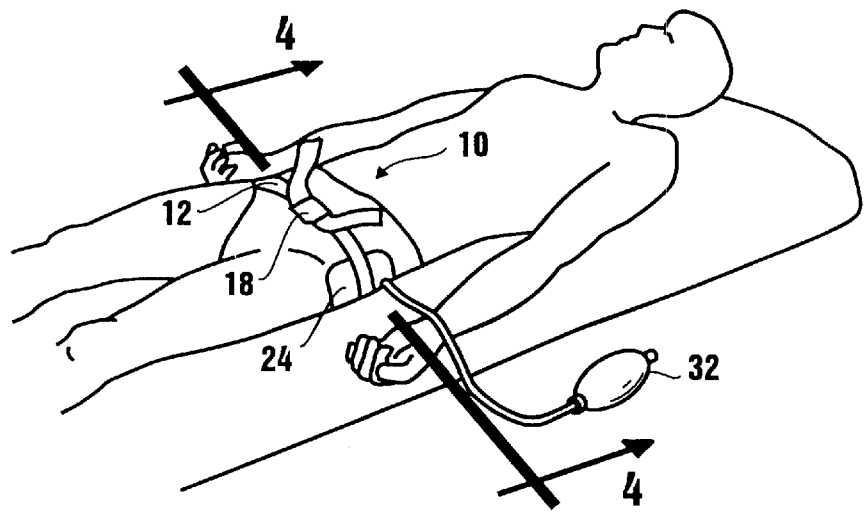
FIG. 1 is a pictorial representation of the device of the present invention shown operationally positioned around the hips of a patient.

The present invention is a device for compressive reduction of the bones of the pelvis. The present invention may be more easily appreciated by initial reference to FIG. 1 where the device is shown operationally positioned around the hips of a patient and generally designated 10.

Figure 2:
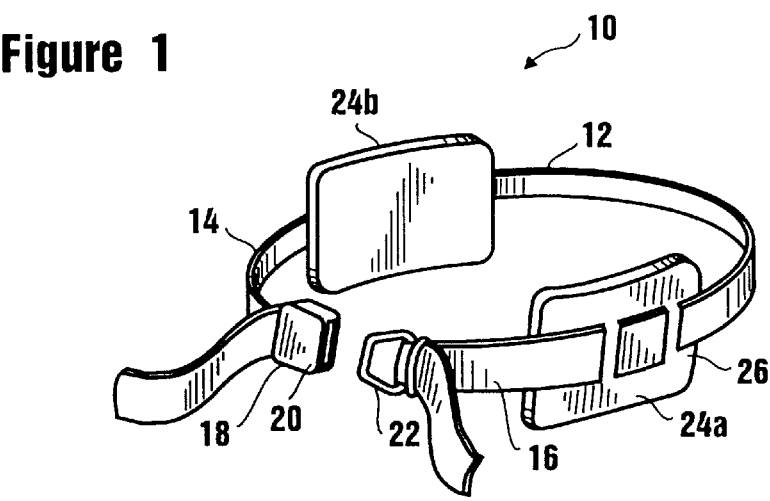
FIG. 2 is a perspective view of the device of the present invention.

The structural details of the device 10, may be better appreciated by reference to FIG. 2 where it may be seen that the device 10 includes a belt 12 having a first end 14 and a second end 16. Preferably, belt 12 is fabricated of a material like nylon fabric, which is washable and sterilizable and also substantially transparent to X-ray radiation. Additionally, it may be seen that the device 10 includes a two-part connector or fastener 18. More specifically, it may be seen that fastener 18 includes a first part 20 and a second part 22. First part 20 is attached to the belt 12 at a selectable distance from first end 14. Similarly, second part 22 is attached to belt 12 at a selectable distance from second end 16. The first part 20 and second part 22 of fastener 18 are interconnectable to attach first end 14 to second end 16 of belt 12. When interconnected in this fashion, the belt 12 has an overall length between first end 14 and second end 16. Importantly, the ability of the first half 20 of the fastener 18 to be selectively distanced from the first end 14 of the belt 12 allows the overall length of the belt 12 to be adjusted. Alternately, the overall length of the belt 12 may be changed by selectively distancing second half 22 of fastener 18 from second end 16 of belt 12.

Generally, the fastener 18 may be of any type that allows first end 14 and second end 14 of the belt 12 to be interconnected, and allows the overall length between first end 14 and second end 16 of the belt 12 to be selectably adjustable. For example, it is possible to implement first half 20 and second half 22 of fastener 18 as complementary VELCRO-type connectors. Preferably, however, first half 20 and second half 22 of fastener 18 are implemented as a quick-release nylon clasp or buckle.

FIG. 2 also shows that the device 10 includes at least two bladders 24 of which bladder 24a and 24b are representative. Each bladder 24 is formed to have a substantially rectangular shape and each is slidingly attached to the belt 12. Each bladder 24 includes one or more loops 26. The loops 26 pass over the belt 12 attaching the bladder 24 to the belt 12. Importantly, the attachment between the bladders 24 and the belt 12 allows the bladders to be slidingly repositioned between first end 14 and second end 16 of belt 12.

Figure 3:
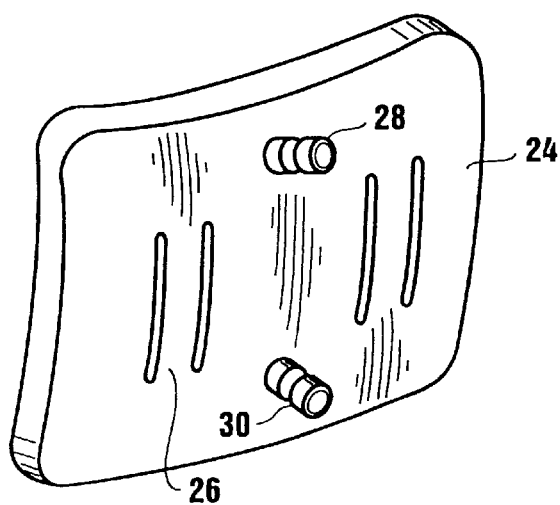
FIG. 3 is a perspective view of a bladder of the present invention.

The details of the bladders 24 are better seen in FIG. 3 where it may be seen that bladder 24 includes a quick-release connector 28 and a pressure relief valve 30. Additionally, it should be appreciated that each bladder 24 is formed to surround an inner chamber (not shown) and that each quick-release connector 28 is attached in fluid communication to the chamber included in the respective bladder 24. Functionally, the quick-release connector 28 allows each bladder 24 to be connected to a pump 32 or other source of fluid pressure. The pump 32, which is preferably a hand-held, bulb-type pump, may then be used to selectively pressurize each chamber of each bladder 24. The pressurization of each bladder 24 causes a corresponding expansion of bladders 24. In this way, the pump 32 may be used to selectively and individually expand each of the bladders 24.

Preferably, bladder 24 is fabricated with an outer layer of a nylon fabric and an inner layer of an inflatable material, such as latex. The combination of the nylon outer layer and latex inner layer result in a bladder 24 which is sterilizable and also substantially transparent to X-ray radiation. Importantly, the material that is used for the manufacture of bladder 24 must be capable of withstanding pressures that are capable of generating combined forces on the belt 12 which exceed five hundred pounds. Each bladder 24 is also preferably formed to include a pressure relief valve 32. Pressure relief valve 30 may be of any type which may be preconfigured to open at a predetermined pressure to prevent over pressurization of the bladder 24.

Operation

In use, the belt 12 of the device 10 is first positioned to encircle the hips of a patient. The bladders 24 are positioned so that at least one bladder 24 is positioned to be substantially adjacent and overlaying each of the patient's hip bones. The first end 20 and second end 22 of the fastener 18 are interconnected holding the belt 12 around the patient's hips. With the belt 12 positioned around the patient's hips, the overall length of the belt 12 is adjusted to tighten the belt 12 around the patent's hips. With the belt 12 tightly positioned to encircle the hips of the patient, the pump 32 is used to selectively inflate each of the bladders 24. As the bladders 24 inflate, the belt 12 applies compressive forces to the pelvic bones of the patient (represented by the arrows 40a and 40b in FIG. 4). The compressive force reduces any separation of the bones of the pelvis and reduces the intra-pelvic volume. The reduction in pelvic volume creates a tamponing effect and diminishes blood loss due to fracture or diastasis of the pelvis. The compressive force is limited to safe levels by the action of the pressure relief valves 30 which prevent over pressurization of the bladders 24. In order to be effective for the purposes of the present invention, however, the compressive forces (40a and 40b) must be greater than approximately five hundred pounds.

Figure 4A:
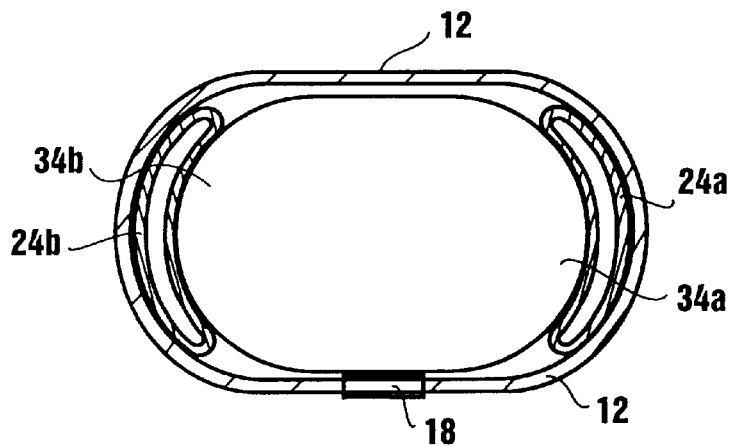
FIG. 4A is a cross-sectional view of the patient and device as seen along the line 4—4 in FIG. 1 with the bladders of the device deflated.

Referring now to FIG. 4A the device 10 is seen positioned around the patient with the deflated bladders 24a,b positioned respectively against the patient's hips 34a,b. With the bladders 24a,b deflated, the bladders 24a,c are properly positioned on the patient and fastener 18 is adjusted to fit the belt 12 snugly, but not to tightly, against the patient. Note that with this configuration there is a generally uniform force distribution which is generated completely around the patient. This force distribution is caused by action of the belt 12 against the patient. This force distribution, however, is significantly altered when the bladders 24a,b are inflated.

Figure 4B:
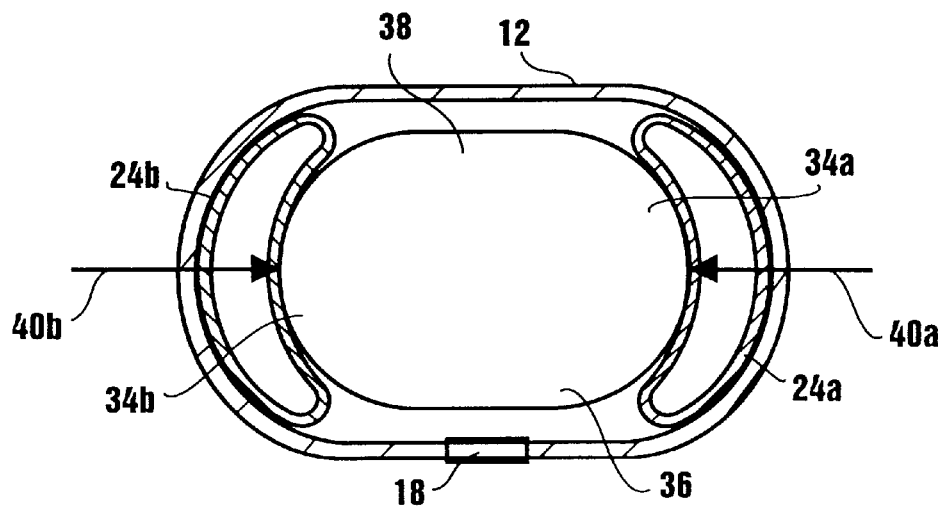
FIG. 4B is a view as in FIG. 4A with the bladders inflated.

In FIG. 4B it can be seen that when the bladders 24a,b are inflated, due to their manufactured configuration (see FIG. 3), the bladders 24a,b will tend to enlarge and elongate, and to thereby define a longitudinal axis which is generally aligned along the length of the belt. Two effects result from their enlargement of the bladders 24a,b. First, the belt 12 is lifted from the abdomen 36 and from the back 38 of the patient. This lifting action significantly reduces, and may even nullify, the force of the belt 12 against the abdomen 36 and back 38 of the patient. Secondly, at the same time, the forces generated by device 10 on the patient are concentrated in the area where the inflated bladders 24a,b are positioned respectively against the hips 34a,b of the patient. Specifically, opposing forces (represented by the arrows 40a and 40b in FIG. 4B) are generated for anatomical reduction of the pelvic bones and, as indicated above, these forces must be greater than approximately five hundred pounds in order to accomplish the purposes of the present invention. Note that while these opposing forces (arrows 40a and 40b) are acting against the hips 34a,b surgical access to the abdomen 36 or back 38 of the patient remains unimpeded.

Subsequent to the application of the device 10, the patient may be moved or manipulated with reduced danger of patient morbidity due to movement of unstable fracture components. Additionally, the device 10 may be left in-place as required for X-rays images, including images of the pelvic bones, are obtained, and may be left in-place during the surgical procedures directed at the abdomen and pelvis.

While the particular pelvic device as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for applying substantial opposing forces against the hips of a patient for anatomical reduction of the pelvic bones of the patient, the method which comprises the steps of:

positioning a first inflatable bladder against a first hip of the patient;

positioning a second inflatable bladder against a second hip of the patient;

retaining said first inflatable bladder and said second inflatable bladder against said respective hips of the patient with a belt, said belt surrounding the patient with said first and said second bladders located between the belt and the patient to restrict movement of said first inflatable bladder relative to said second inflatable bladder;

inflating said first inflatable bladder and said second inflatable bladder to enlarge both said bladders and substantially lift said belt from the abdomen and the back of the patient while simultaneously generating opposing forces by said bladders against the respective first and second hip of the patient for anatomical reduction of the pelvic bones of the patient, with each of said opposing forces having a magnitude greater than approximately five hundred pounds.

2. A method as recited in claim 1 further comprising the step of adjusting said belt to snugly hold said first and second bladders against said respective hips prior to said inflating step.

3. A method as recited in claim 1 wherein said inflating step is accomplished using a hand-held bulb-type pump.

* * * * *